(12) United States Patent
Kondo et al.

(10) Patent No.: US 8,497,114 B2
(45) Date of Patent: Jul. 30, 2013

(54) ANTI-OBESITY AGENT, ANTI-OBESITY FOOD OR BEVERAGE, GLUCOSE TOLERANCE-AMELIORATING AGENT, AND FOOD OR BEVERAGE FOR AMELIORATION OF GLUCOSE TOLERANCE

(75) Inventors: Shizuki Kondo, Yokohama (JP); Kanetada Shimizu, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 13/395,824

(22) PCT Filed: Sep. 17, 2010

(86) PCT No.: PCT/JP2010/066193
§ 371 (c)(1), (2), (4) Date: Mar. 13, 2012

(87) PCT Pub. No.: WO2011/034166
PCT Pub. Date: Mar. 24, 2011

(65) Prior Publication Data
US 2012/0171167 A1    Jul. 5, 2012

(30) Foreign Application Priority Data
Sep. 17, 2009    (JP) ................. 2009-215836

(51) Int. Cl.
*C12N 1/12* (2006.01)
*A01N 63/00* (2006.01)

(52) U.S. Cl.
USPC ....................... 435/252.1; 424/93.4

(58) Field of Classification Search
None
See application file for complete search history.

(56) References Cited

FOREIGN PATENT DOCUMENTS

| JP | 61271223 A | 12/1986 |
|---|---|---|
| JP | 2004137167 A | 5/2004 |
| JP | 2005522216 A | 7/2005 |
| WO | 0245732 A1 | 6/2002 |
| WO | 2002045732 A1 | 6/2002 |
| WO | 03087344 A1 | 10/2003 |

OTHER PUBLICATIONS

Totani, N. et al., Effects of Bifidobacterium bifidum on fatty/diabetic animals, Igaku no Ayumi, Apr. 26, 2003, pp. 273-274, vol. 205, No. 4.

Delany, J. P. et al., Conjugated linoleic acid rapidly reduces body fat content in mice without affecting energy intake, The American Physiological Society, 1999, pp. R1172-R1179, vol. 276.

Tsuboyama-Kasaoka, N. et al., Conjugated Linoleic Acid Supplementation Reduces Adipose Tissue by Apoptosis and Develops Lipodystrophy in Mice, Diabetes, Sep. 2000, pp. 1534-1542, vol. 49.

Riserus, U. et al., Effects of cis-9, trans-11 conjugated linoleic acid supplementation on insulin sensitivity, lipid peroxidation, and proinflammatory markers in obese men 1-3, The American Journal of Clinical Nutrition, 2004, pp. 279-283, vol. 80.

Tsuji, E. et al., The Current Status of Linoleic Acid Intake, Shishitsu Eiyougaku [Lipid Nutrition], Department of Nutrition Management, Faculty of Health Science, Hyogo University, 2002, pp. 25-31, vol. 11.

Tahri, K. et al., Effects of three strains of bifidobacteria on cholesterol, Letters in Applied Microbiology, Sep. 1995, pp. 149-151, vol. 21, No. 3.

Cani, P. D. et al., Selective increases of bifidobacteria in gut microflora improve high-fat-diet-induced diabetes in mice through a mechanism associated with endotoxaemia, Diabetologia, 2007, pp. 2374-2383, vol. 50, No. 11.

Kondo, S. et al., Antiobesity Effects of bifidobacterium breve Strain B-3 Supplementation in a Mouse Model with High-Fat Diet-Induced Obesity, Bioscience, Biotechnology, and Biochemistry, Aug. 23, 2010, pp. 1656-1661, vol. 74, No. 8.

International Search Report issued in International Application No. PCT/JP2010/066193, mailed Nov. 22, 2010, 6 pages.

Japanese Official Action issued in Japanese Patent Application No. 2011-508756, mailed Jun. 21, 2011, 5 pages.

Examination Report issued in New Zealand patent application No. 598751; Feb. 18, 2013; 2 pages; Intellectual Property Office of New Zealand.

Lye et al., The Improvement of Hypertension by Probiotics: Effects on Cholesterol, Diabetes, Renin, and Phytoestrogens, Int. J. Mol. Sci., 2009, 10, 3755-3775.

*Primary Examiner* — Jennifer Pitrak McDonald
*Assistant Examiner* — Qing Xu
(74) *Attorney, Agent, or Firm* — Wood, Herron & Evans, LLP (57) ABSTRACT

An anti-obesity agent or a glucose tolerance-ameliorating agent containing a bacterium belonging to the genus *Bifidobacterium* as an active ingredient, wherein the bacterium belonging to the genus *Bifidobacterium* exhibits a conversion rate from linoleic acid into conjugated linoleic acid of not more than 10%. The present invention is able to provide an anti-obesity agent and a glucose tolerance-ameliorating agent that are effective for the prevention or treatment of obesity or the amelioration of glucose tolerance and also exhibit superior safety, as well as providing foods or beverages containing these agents. Further, the present invention is also able to provide a bacterium of the genus *Bifidobacterium*, and in particular a *Bifidobacterium breve*, that is effective for the prevention or treatment of obesity or the amelioration of glucose tolerance and also exhibits superior safety, as well as providing a pharmaceutical composition containing this bacterium.

3 Claims, 2 Drawing Sheets

ANTI-OBESITY AGENT, ANTI-OBESITY FOOD OR BEVERAGE, GLUCOSE TOLERANCE-AMELIORATING AGENT, AND FOOD OR BEVERAGE FOR AMELIORATION OF GLUCOSE TOLERANCE

TECHNICAL FIELD

The present invention relates to an anti-obesity agent, an anti-obesity food or beverage, a glucose tolerance-ameliorating agent, and a food or beverage for the amelioration of glucose tolerance which contain a specific *Bifidobacterium breve* as an active ingredient.

Priority is claimed on Japanese Patent Application No. 2009-215836, filed Sep. 17, 2009, the content of which is incorporated herein by reference.

BACKGROUND ART

As the lifestyle of the Japanese people becomes more westernized and the aging of the population continues to progress rapidly, the number of patients with lifestyle-related diseases such as ischemic heart disease, cerebrovascular disease and diabetes continues to increase. One of the major causes of these types of lifestyle-related diseases is obesity, and the importance of preventing and remedying obesity is widely stressed. Further, obesity is also seen as undesirable from the viewpoints of appearance and beauty, and there is much interest in dieting for the purpose of preventing or remedying obesity.

Against this type of background of heightened awareness of obesity, a diagnostic criterion known as "metabolic syndrome" has been identified as increasing the probability of the future onset of lifestyle-related disease, and measurement of the waist circumference is used in medical checkups with the purpose of preventing and/or remedying metabolic syndrome.

Examples of methods that are conventionally used for addressing obesity include dietary treatments (dietary restriction and fasting), exercise-based treatments (promoting energy consumption through exercise), and drug-based treatments. Examples of the drugs currently used in drug-based treatments include Orlistat, which inhibits the absorption of fat in the intestinal tract (such as the drugs "Xenical" (a registered trademark) manufactured by Roche Ltd., and "Alli" (a registered trademark) manufactured by Glaxo-SmithKline plc.), and Acarbose, which is an inhibitor of the glycolytic enzyme ($\alpha$-glucosidase) (such as the drug "Glucobay" (a registered trademark) manufactured by Bayer AG).

However, excessive use of these treatments can cause a number of problems, including impairment of the health of the patient, weight increase due to rebound, and difficulty in achieving continuous or long-term treatment. Particularly in the case of the drug-based methods, side effects tend to also be a problem. Further, the drugs used in the drug-based treatments are pharmaceutical drugs, and are not particularly easy to use.

Tests on inhibiting obesity using microbes such as lactic acid bacteria have been previously reported. For example, Non-Patent Document 1 reports that when a feed containing 10% of live dried *Bifidobacterium bifidum* G9-1 was fed to exogenously hypercholesterolemic (ExHC) rats, obese (Wistar fatty) rats, and obese and diabetic (KK-A$^y$) mice, the levels of triacylglycerol and cholesterol in the blood and liver decreased. However, when the above bacterial strain is used, a large amount of the bacteria must be mixed into the feed to obtain the above effects, and ensuring routine and continuous ingestion of the effective amount is difficult.

Furthermore, conjugated linoleic acid (CLA) is known to exhibit physiological activity including an anti-obesity action. For example, Non-Patent Document 2 reports an animal study in which mixing CLA into feed in amounts of 0, 0.25, 0.5 and 1% revealed that, at amounts of 0.5% or higher, body weight and body fat were reduced in a concentration-dependent manner.

In relation to CLA, it is known that bacteria such as those of the genus *Bifidobacterium* have the ability to convert linoleic acid (LA) into CLA (CLA conversion function), and various techniques have been proposed that utilize these bacteria. For example, Patent Document 1 discloses that the *Bifidobacterium breve* CBG-C2, *Bifidobacterium pseudocatenulatum* CBG-C4 and *Enterococcus faecium* CBG-05 all exhibit superior CLA conversion functonality, and Table 1 discloses that the *Bifidobacterium breve* CBG-C2 converted LA to CLA with a high CLA conversion rate of 54.7%. Further, Patent Document 1 also discloses the use of CLA-generating compositions comprising these bacterial strains as active ingredients in the prevention or treatment of diseases that are inhibited by CLA (such as cancer, arterial sclerosis, diabetes and obesity).

However, when CLA or bacteria having a superior CLA conversion function are administered as part of a diet aimed at either treating obesity or preventing obesity, there is a danger that side effects may occur.

As an example of these CLA side effects, Non-Patent Document 3 reports that when 1% of CLA was mixed with mice feed and administered over an 8-month period, atrophy of the adipose tissue, an increase in the insulin level, and a reduction in glucose tolerance were all observed. Further, Non-Patent Document 4 reports that when humans ingested approximately 3 g of CLA daily over a continuous period, glucose tolerance tended to worsen, as evidenced by a decrease in insulin sensitivity and an increase in oxidation markers in the urine.

Furthermore, the average LA ingestion amount by Japanese people is approximately 11 g (see Non-Patent Document 5), and therefore if bacteria having a high CLA conversion function is administered, CLA will be produced in large amounts. For example, if 11 g of LA is converted to CLA with the above-mentioned conversion rate of 54.7%, then 6.02 g of CLA will be produced. If a large amount of CLA is produced in this manner, then the above-mentioned side effects become a concern.

CITATION LIST

Patent Documents

[Patent Document 1] Published Japanese Translation No. 2005-522216 of PCT

Non-Patent Documents

[Non-Patent Document 1] "Effects of bifidobacteria on obese and diabetic animal models", Igaku no ayumi [Progress in Medicine], 205(4), 273 to 274 (2003)
[Non-Patent Document 2] "Conjugated linoleic acid rapidly reduces body fat content in mice without affecting energy intake", The American Journal of Physiology, 276, 1172 to 1179 (1999)
[Non-Patent Document 3] "Conjugated linoleic acid supplementation reduces adipose tissue by apoptosis and develops lipodystrophy in mice", DIABETES, 49, 1534 to 1541 (2000)

[Non-Patent Document 4] "Effects of cis-9, trans-11 conjugated linoleic acid supplementation on insulin sensitivity, lipid peroxidation, and proinflammatory markers in obese men", The American Journal of Clinical Nutrition, 80, 279 to 283 (2004)

[Non-Patent Document 5] "The current state of linoleic acid ingestion", Shishitsu Eiyougaku [Lipid Nutrition], 11, 25 to 31 (2002)

DISCLOSURE OF INVENTION

Problems to be Solved by the Invention

The present invention takes the above circumstances into consideration, with an object of providing an anti-obesity agent and a glucose tolerance-ameliorating agent that are effective for the prevention or treatment of obesity or the amelioration of glucose tolerance and also exhibit superior safety, as well as providing foods or beverages containing these agents.

Means to Solve the Problems

As a result of intensive investigation, the inventors of the present invention discovered that *Bifidobacterium breve*, which exhibits a low conversion rate into conjugated linoleic acid, has an anti-obesity action and a glucose tolerance-ameliorating action that are independent of conjugated linoleic acid, and on the basis of this finding, they were able to complete the present invention.

In order to achieve the object described above, the present invention adopts the forms described below.

(1) An anti-obesity agent containing, as an active ingredient, a *Bifidobacterium breve* for which the conversion rate from linoleic acid into conjugated linoleic acid, determined in accordance with the procedure described below, is not more than 10%.

Bacterial cells of the above *Bifidobacterium breve* are suspended at a concentration of $2\times10^7$ CFU/mL in a liquid medium containing an added concentration of linoleic acid of 500 µg/mL, and after incubation for 48 hours at 37° C., the amount of produced conjugated linoleic acid is measured, and the conversion rate (%) from linoleic acid into conjugated linoleic acid is determined from the formula below.

Conversion rate (%)=(produced conjugated linoleic acid/added linoleic acid)×100

(2) The anti-obesity agent according to (1), wherein the *Bifidobacterium breve* is *Bifidobacterium breve* MCC 1274 and/or *Bifidobacterium breve* ATCC 15700.

(3) An anti-obesity food or beverage containing the anti-obesity agent according to (1) or (2).

(4) A glucose tolerance-ameliorating agent containing, as an active ingredient, a *Bifidobacterium breve* for which the conversion rate from linoleic acid into conjugated linoleic acid, determined in accordance with the procedure described below, is not more than 10%.

Bacterial cells of the above *Bifidobacterium breve* are suspended at a concentration of $2\times10^7$ CFU/mL in a liquid medium containing an added concentration of linoleic acid of 500 µg/mL, and after incubation for 48 hours at 37° C., the amount of produced conjugated linoleic acid is measured, and the conversion rate (%) from linoleic acid into conjugated linoleic acid is determined from the formula below.

Conversion rate (%)=(produced conjugated linoleic acid/added linoleic acid)×100

(5) The glucose tolerance-ameliorating agent according to (4), wherein the *Bifidobacterium breve* is *Bifidobacterium breve* MCC 1274 and/or *Bifidobacterium breve* ATCC 15700.

(6) A food or beverage for ameliorating glucose tolerance, containing the glucose tolerance-ameliorating agent according to (4) or (5).

Furthermore, the present invention includes the aspects listed below.

<1> A bacterium of genus *Bifidobacterium*, for use in anti-obesity treatment or amelioration of glucose tolerance, wherein the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of $2\times10^7$ CFU/mL in a liquid medium containing an added concentration of linoleic acid of 500 µg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<2> Use of a bacterium of genus *Bifidobacterium* for anti-obesity treatment or amelioration of glucose tolerance, wherein the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of $2\times10^7$ CFU/mL in a liquid medium containing an added concentration of linoleic acid of 500 µg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<3> Use of a bacterium of genus *Bifidobacterium* for producing a composition, and preferably a pharmaceutical composition, for anti-obesity treatment or amelioration of glucose tolerance, wherein the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of $2\times10^7$ CFU/mL in a liquid medium containing an added concentration of linoleic acid of 500 µg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<4> A pharmaceutical composition containing a bacterium of genus *Bifidobacterium* used for anti-obesity treatment or amelioration of glucose tolerance, and a pharmaceutically acceptable carrier, wherein the bacterium of genus *Bifidobacterium* exhibits a conversion rate from linoleic acid into conjugated linoleic acid of not more than 10%, the conversion rate being determined by suspending bacterial cells of the bacterium of genus *Bifido-*

*bacterium* at a concentration of 2×10⁷ CFU/mL in a liquid medium containing an added concentration of linoleic acid of 500 μg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<5> Use of a pharmaceutical composition containing a bacterium of genus *Bifidobacterium* and a pharmaceutically acceptable carrier for anti-obesity treatment or amelioration of glucose tolerance, wherein
the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of 2×10⁷ CFU/mL in a liquid medium containing an added concentration of linoleic acid of 500 μg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<6> The bacterium of genus *Bifidobacterium* according to <1>, wherein the bacterium of genus *Bifidobacterium* is a *Bifidobacterium breve*.

<7> The bacterium of genus *Bifidobacterium* according to <6>, wherein the *Bifidobacterium breve* is selected from the group consisting of *Bifidobacterium breve* MCC 1274 (FERM BP-11175) and *Bifidobacterium breve* ATCC 15700.

<8> The use of a bacterium of genus *Bifidobacterium* according to <2> or <3>, wherein the bacterium of genus *Bifidobacterium* is a *Bifidobacterium breve*.

<9> The use of a bacterium of genus *Bifidobacterium* according to <8>, wherein the *Bifidobacterium breve* is selected from the group consisting of *Bifidobacterium breve* MCC 1274 (FERM BP-11175) and *Bifidobacterium breve* ATCC 15700.

<10> The pharmaceutical composition according to <4>, wherein the bacterium of genus *Bifidobacterium* is a *Bifidobacterium breve*.

<11> The pharmaceutical composition according to <10>, wherein the *Bifidobacterium breve* is selected from the group consisting of *Bifidobacterium breve* MCC 1274 (FERM BP-11175) and *Bifidobacterium breve* ATCC 15700.

<12> The use of a pharmaceutical composition according to <5>, wherein the bacterium of genus *Bifidobacterium* is a *Bifidobacterium breve*.

<13> The use of a pharmaceutical composition according to <12>, wherein the *Bifidobacterium breve* is selected from the group consisting of *Bifidobacterium breve* MCC 1274 (FERM BP-11175) and *Bifidobacterium breve* ATCC 15700.

<14> An anti-obesity agent or glucose tolerance-ameliorating agent containing a bacterium of genus *Bifidobacterium* as an active ingredient, wherein
the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of 2×10⁷ CFU/mL in a liquid medium containing an added concentration of linoleic acid of 500 μg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<15> The anti-obesity agent or glucose tolerance-ameliorating agent according to <14>, wherein the bacterium of genus *Bifidobacterium* is a *Bifidobacterium breve*.

<16> The anti-obesity agent or glucose tolerance-ameliorating agent according to <15>, wherein the *Bifidobacterium breve* is selected from the group consisting of *Bifidobacterium breve* MCC 1274 (FERM BP-11175) and *Bifidobacterium breve* ATCC 15700.

<17> An anti-obesity food or beverage or a food or beverage for ameliorating glucose tolerance, containing the anti-obesity agent or glucose tolerance-ameliorating agent according to any one of <14> to <16>.

<18> A bacterial strain that is *Bifidobacterium breve* MCC 1274 (FERM BP-11175).

<19> A bacterial strain selected from the group consisting of *Bifidobacterium breve* MCC 1274 (FERM BP-11175) and *Bifidobacterium breve* ATCC 15700, for use in anti-obesity treatment or amelioration of glucose tolerance.

<20> Use of a bacterial strain selected from the group consisting of *Bifidobacterium breve* MCC 1274 (FERM BP-11175) and *Bifidobacterium breve* ATCC 15700 for anti-obesity treatment or amelioration of glucose tolerance.

<21> Use of a bacterial strain selected from the group consisting of *Bifidobacterium breve* MCC 1274 (FERM BP-11175) and *Bifidobacterium breve* ATCC 15700 for producing a composition for anti-obesity treatment or amelioration of glucose tolerance.

<22> A pharmaceutical composition containing a bacterial strain selected from the group consisting of *Bifidobacterium breve* MCC 1274 (FERM BP-11175) and *Bifidobacterium breve* ATCC 15700 for use in anti-obesity treatment or amelioration of glucose tolerance, and a pharmaceutically acceptable carrier.

<23> Use of a pharmaceutical composition containing a bacterial strain selected from the group consisting of *Bifidobacterium breve* MCC 1274 (FERM BP-11175) and *Bifidobacterium breve* ATCC 15700, and a pharmaceutically acceptable carrier, for anti-obesity treatment or amelioration of glucose tolerance.

<24> An anti-obesity agent or glucose tolerance-ameliorating agent containing, as an active ingredient, a bacterial strain selected from the group consisting of *Bifidobacterium breve* MCC 1274 (FERM BP-11175) and *Bifidobacterium breve* ATCC 15700.

<25> A method of treating or preventing obesity that involves administering an amount of a bacterium of genus *Bifidobacterium* that is effective in treating or preventing obesity to a subject that requires treatment or prevention of obesity, wherein
the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of 2×10⁷ CFU/mL in a liquid medium containing an added concentration of linoleic acid of 500 μg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<26> The method of treating or preventing obesity according to <25>, wherein the bacterium of genus *Bifidobacterium* is a *Bifidobacterium breve*.

<27> The method of treating or preventing obesity according to <26>, wherein the *Bifidobacterium breve* is selected from the group consisting of *Bifidobacterium breve* MCC 1274 (FERM BP-11175) and *Bifidobacterium breve* ATCC 15700.

<28> A method of ameliorating glucose tolerance that involves administering an amount of a bacterium of genus *Bifidobacterium* that is effective in ameliorating glucose tolerance to a subject that requires amelioration of glucose tolerance, wherein the bacterium of genus *Bifidobacterium* exhibits a conversion rate from linoleic acid into conjugated linoleic acid of not more than 10%, the conversion rate being determined by suspending bacterial cells of the bacterium of genus *Bifidobacterium* at a concentration of $2 \times 10^7$ CFU/mL in a liquid medium containing an added concentration of linoleic acid of 500 µg/mL, performing incubation for 48 hours at 37° C., subsequently measuring the amount of produced conjugated linoleic acid, and then calculating the conversion rate (%) from linoleic acid into conjugated linoleic acid from the formula:

Conversion rate (%)=(produced conjugated linoleic acid/added linoleic acid)×100.

<29> The method of ameliorating glucose tolerance according to <28>, wherein the bacterium of genus *Bifidobacterium* is a *Bifidobacterium breve*.

<30> The method of ameliorating glucose tolerance according to <29>, wherein the *Bifidobacterium breve* is selected from the group consisting of *Bifidobacterium breve* MCC 1274 (FERM BP-11175) and *Bifidobacterium breve* ATCC 15700.

<31> A method of treating or preventing obesity that involves administering a bacterial strain selected from the group consisting of *Bifidobacterium breve* MCC 1274 (FERM BP-11175) and *Bifidobacterium breve* ATCC 15700, in an amount that is effective in treating or preventing obesity, to a subject that requires treatment or prevention of obesity.

<32> A method of ameliorating glucose tolerance that involves administering a bacterial strain selected from the group consisting of *Bifidobacterium breve* MCC 1274 (FERM BP-11175) and *Bifidobacterium breve* ATCC 15700, in an amount that is effective in ameliorating glucose tolerance, to a subject that requires amelioration of glucose tolerance.

Effect of the Invention

The present invention is able to provide an anti-obesity agent and a glucose tolerance-ameliorating agent that are effective for the prevention or treatment of obesity or the amelioration of glucose tolerance and also exhibit superior safety, as well as providing foods or beverages containing these agents. Further, the present invention is also able to provide a bacterium of genus *Bifidobacterium*, and particularly a *Bifidobacterium breve*, that is effective for the prevention or treatment of obesity or the amelioration of glucose tolerance or insulin resistance and also exhibits superior safety, as well as a pharmaceutical composition containing the bacterium of genus *Bifidobacterium*.

EMBODIMENTS FOR CARRYING OUT THE INVENTION

A *Bifidobacterium breve* (hereinafter frequently abbreviated as "*B. breve*") belonging to the genus *Bifidobacterium* that is used in the present invention is a *B. breve* for which the conversion rate from linoleic acid (LA) into conjugated linoleic acid (CLA) (hereinafter also referred to as the "CLA conversion rate"), determined in accordance with the procedure described below, is not more than 10%.

Bacterial cells of the above *B. breve* are suspended at a concentration of $2 \times 10^7$ CFU/mL in a liquid medium containing an added concentration of LA of 500 µg/mL, and after incubation for 48 hours at 37° C., the amount of produced CLA is measured, and the CLA conversion rate (%) is determined from the formula below.

Conversion rate (%)=(amount of produced CLA/ amount of added LA)×100

The above-mentioned "amount of produced CLA" can be measured, for example, using the procedure described below.

First, following the 48 hours of incubation, the above liquid medium is subjected to centrifugal separation.

The supernatant is recovered, a volume of isopropyl alcohol twice that of the supernatant is added to the supernatant and mixed, a volume of hexane 1.5 times that of the supernatant is then added to the mixture, and after mixing for 3 minutes, the mixture is left to settle and the hexane layer is recovered. The absorbance of the hexane layer at 233 nm is measured, and based on a comparison with standard materials (cis-9, trans-11 conjugated linoleic acid), the CLA concentration (µg/mL) within the hexane layer is determined and the amount of CLA (µg) contained within the above supernatant is calculated.

Meanwhile, to the residue left following recovery of the supernatant is added and mixed an amount of distilled water 5 times that of the residue, thus forming a suspension. A volume of isopropyl alcohol twice that of the suspension is added to the suspension and mixed, a volume of hexane 1.5 times that of the suspension is then added to the mixture, and after mixing for 3 minutes, the mixture is left to settle and the hexane layer is recovered. The CLA concentration (µg/mL) within the hexane layer is determined in the same manner as that described above, and the amount of CLA (µg) contained within the residue is calculated.

The total of the amounts of CLA contained within the supernatant and the residue is recorded as the "amount of produced CLA".

The liquid medium may be any medium capable of culturing *B. breve*, and may be selected appropriately from conventional liquid media. Specific examples include the MRS (de Man Rogossa Sharpe) medium, ABCM (Anaerobic Bacterial Culture Medium) and RCA (Reinforced Clostridial Agar) medium.

The above description describes an example in which cis-9, trans-11 conjugated linoleic acid is used as the standard material, but the calculated amounts of CLA are substantially the same even if a different isomer such as trans-10, cis-12 conjugated linoleic acid is used.

The CLA conversion rate is an indicator of the magnitude of the CLA conversion function (the ability to convert LA into CLA) possessed by the *B. breve*.

*B. breve* that exhibits a CLA conversion rate of not more than 10% (hereinafter also referred to as "low CLA conversion *B. breve*") has an anti-obesity action that does not depend on CLA.

An "anti-obesity action" describes an action that prevents or ameliorates obesity by suppressing weight gain and/or suppressing increases in body fat.

In the present invention, the term "obesity" refers not only to the simple state of having a large body weight, but also to a state in which the proportion of adipose tissue among the structural components of the body is abnormally large.

In recent years it has been reported that, in terms of the accumulation of subcutaneous fat and visceral fat, visceral fat obesity, in which the fat accumulates between the organs, is more likely to be associated with adult diseases such as high blood pressure, hyperlipidemia and diabetes than subcutaneous fat obesity, in which the fat accumulates within the subcutaneous tissue. As illustrated in test example 2 below, low CLA conversion *B. breve* has an inhibiting effect on body weight increase, and in particular, has an effect of inhibiting the accumulation of visceral fat. Accordingly, foods and beverages containing the anti-obesity agent and glucose tolerance-ameliorating agent of the present invention are effective in the prevention and treatment of the above diseases.

Furthermore, because low CLA conversion *B. breve* has a limited ability to convert LA into CLA, there is minimal danger of the side effects caused by CLA such as atrophy of the adipose tissue, increase in the insulin level, and reduction in glucose tolerance. In other words, if, as disclosed in the above-mentioned Non-Patent Document 5, the average LA ingestion amount by Japanese people is approximately 11 g, and the CLA conversion rate is high, then LA is converted to CLA in vivo, and there is considerable danger of side effects caused by CLA, but because the *B. breve* used in the present invention has a low CLA conversion rate, it is surmised that side effects caused by CLA will not occur, making the treatment extremely safe.

Accordingly, the anti-obesity agent of the present invention can be ingested safely, and by blending the anti-obesity agent into a food or beverage, and then administering an effective amount of the food or beverage to an obese patient or a healthy human or pet that is in need of dieting, either on a day-to-day basis or over an extended period if required, an anti-obesity action can be realized.

Further, low CLA conversion *B. breve* does not cause abnormal glucose tolerance, which is one of the known side effects of CLA, and as illustrated in test example 2 below, actually has a glucose tolerance-ameliorating action and an insulin resistance-ameliorating action.

Accordingly, the glucose tolerance-ameliorating agent of the present invention can be ingested safely, and by blending the glucose tolerance-ameliorating agent into a food or beverage, and then administering an effective amount of the food or beverage to a diabetic patient or a healthy human or pet that is in need of glucose tolerance amelioration, either on a day-to-day basis or over an extended period if required, a glucose tolerance-ameliorating action and an insulin resistance-ameliorating action can be realized.

The low CLA conversion *B. breve* used in the present invention may be any *B. breve* for which the CLA conversion rate is not more than 10%, and for example, a new *B. breve* strain isolated and identified from a sample such as the feces of a human infant or a conventional *B. breve* strain may be subjected to measurement of the CLA conversion rate using the procedure described above, and any strain for which the measured conversion rate is 10% or less may then be selected appropriately.

Examples of low CLA conversion *B. breve* strains include *B. breve* MCC 1274 and *B. breve* ATCC 15700.

*B. breve* MCC 1274 is a bacterial strain belonging to the genus *Bifidobacterium* that was acquired and identified by the applicants of the present invention using the procedure outlined below, and was deposited with the International Patent Organism Depositary of the National Institute of Advanced Industrial Science and Technology (Central 6, 1-1-1 Higashi, Tsukuba City, Ibaraki Prefecture, Japan (zip code: 305-8566)) on Aug. 25, 2009 (accession number: FERM BP-11175).

(Acquisition and Identification of *B. breve* MCC 1274)

Using feces from a Japanese infant as a sample, the sample was diluted with an anaerobic diluent (a diluent disclosed on page 322 of "Chounaikin no Sekai" [*The World of Enteric Bacteria*] (by Tomotari Mitsuoka, published by Soubunsha Co., Ltd., 1980), applied to a flat plate of a BL agar medium (disclosed on page 319 of "Chounaikin no Sekai"), and then incubated anaerobically at 37° C. for 72 hours. Among the resulting colonies, those strains that exhibited morphological characteristics of a *Bifidobacterium*, were Gram positive, and exhibited a rod-shaped, club-shaped or Y-shaped bacterial cell when an applied specimen was observed under a microscope were collected and applied in streaks to a BL agar medium, and anaerobic incubation was then repeated using the same method as that described above to obtain the pure isolated bacterial strains. The above-mentioned bacterial strain was named *B. breve* MCC 1274.

The bacteriological properties of *B. breve* MCC 1274 were investigated, including the cell shape, motility, spore formation, Gram staining, catalase activity, gas production from glucose, and fermentation of sugars. Evaluation of the fermentation of sugars was performed using an API 50CH kit (manufactured by bioMerieux, Japan), with determinations made in accordance with the method disclosed in the manual provided with the kit. In other words, following incubation overnight, the bacterial liquid was used to inoculate each of the substrates, the substrates were then incubated at 37° C. inside an anaerobic glove box, and on the seventh day of incubation, the sugar fermentation state of each of the substrates was determined The results are shown in Table 1.

TABLE 1

Bacteriological properties of *Bifidobacterium breve* MCC 1274

| | | MCC 1274 |
|---|---|---|
| 1 | Cell shape | Pleomorphic rod |
| 2 | Motility | None |
| 3 | Spore formation | None |
| 4 | Gram staining | Positive |
| 5 | Catalase activity | − |
| 6 | Gas production from glucose | − |
| 7 | Sugar fermentation | |
| | (1) Control | − |
| | (2) Glycerol | − |
| | (3) Erythritol | − |
| | (4) D-Arabinose | ± |
| | (5) L-Arabinose | − |
| | (6) Ribose | + |
| | (7) D-Xylose | − |
| | (8) L-Xylose | − |
| | (9) Adonitol | − |
| | (10) β-Methyl-xyloside | − |

TABLE 1-continued

Bacteriological properties of *Bifidobacterium breve* MCC 1274

| | MCC 1274 |
|---|---|
| (11) Galactose | + |
| (12) D-Glucose | + |
| (13) D-Fructose | + |
| (14) D-Mannitol | + |
| (15) L-Sorbose | − |
| (16) Rhamnose | − |
| (17) Dulcitol | − |
| (18) Inositol | − |
| (19) Mannitol | + |
| (20) Sorbitol | + |
| (21) α-Methyl-D-mannose | ± |
| (22) α-Methyl-D-glucose | + |
| (23) N-acetylglucosamine | + |
| (24) Amygdalin | + |
| (25) Arbutin | + |
| (26) Esculin | + |
| (27) Salicin | + |
| (28) Cellobiose | + |
| (29) Maltose | + |
| (30) Lactose | + |
| (31) Melibiose | + |
| (32) Saccharose | + |
| (33) Trehalose | + |
| (34) Inulin | − |
| (35) Melezitose | + |
| (36) D-Raffinose | + |
| (37) Amidon | + |
| (38) Glycogen | − |
| (39) Xylitol | + |
| (40) β-Gentioblose | + |
| (41) D-Turanose | + |
| (42) D-Lyxose | − |
| (43) D-Tagatose | − |
| (44) D-Fucose | − |
| (45) L-Fucose | + |
| (46) D-Arabitol | − |
| (47) L-Arabitol | − |
| (48) Gluconate | − |
| (49) 2-keto-glueonate | − |
| (50) 5-keto-gluconate | ± |

Subsequently, in order to investigate the genetic characteristics of *B. breve* MCC 1274, the 16S rRNA genetic base sequencing of the above bacterial strain was identified using conventional methods. Determination of the 16S rRNA genetic base sequence of *B. breve* MCC 1274 using BLAST analysis to perform a homology search of the base sequence within the database of the U.S. National Center for Biotechnology Information (NCBI) revealed 99% homology with the standard *B. breve* strain known as *B. breve* CM 1192$^T$, indicating the strain was a *Bifidobacterium breve*.

The above results confirmed that *Bifidobacterium breve* MCC 1274 had the bacteriological properties of a *Bifidobacterium breve*, and was a bacterial strain belonging to the species *Bifidobacterium breve*.

The low CLA conversion *B. breve* that the anti-obesity agent or glucose tolerance-ameliorating agent of the present invention includes as an active ingredient may be either a single bacterial strain or two or more strains.

Further, the anti-obesity agent or glucose tolerance-ameliorating agent of the present invention may be composed solely of the above-mentioned active ingredient, or may be a composition or pharmaceutical composition containing the active ingredient and other optional components besides the active ingredient. There are no particular limitations on these optional components provided they are pharmaceutically acceptable, and any of the additives (such as the pharmaceutical carriers described below) typically added to pharmaceutical compositions may be included.

The present invention provides a method of treating or preventing obesity that involves administering a *B. breve* according to the present invention, in an amount that is effective in treating or preventing obesity, to a subject that requires treatment or prevention of obesity.

Further, the present invention also provides a method of ameliorating glucose tolerance that involves administering a *B. breve* according to the present invention, in an amount that is effective in ameliorating glucose tolerance, to a subject that requires amelioration of glucose tolerance.

In this description, "treatment" of obesity refers to the administration of the anti-obesity agent of the present invention for the purpose of reducing or maintaining the body weight of a subject. One possible result of this treatment may be a reduction in the body weight of the subject compared with the body weight of the subject immediately prior to the start of administration of the anti-obesity agent of the present invention. Further, another possible result of the treatment may be a suppression of the increase in body weight of the subject compared with the body weight increase of the subject immediately prior to the start of administration of the anti-obesity agent of the present invention.

Moreover, "prevention" of obesity refers to the administration of the anti-obesity agent of the present invention for the purpose of reducing or maintaining the body weight of a subject at risk of obesity. One possible result of this prevention may involve maintaining or reducing the body weight of the "subject at risk of obesity" compared with the body weight of the subject immediately prior to the start of administration of the anti-obesity agent of the present invention. Further, another possible result of the prevention may be a suppression of the increase in body weight of the subject compared with the body weight increase of the subject immediately prior to the start of administration of the anti-obesity agent of the present invention.

In this description, "amelioration" of the glucose tolerance refers to the administration of the glucose tolerance-ameliorating agent of the present invention for the purpose of maintaining or improving the glucose tolerance of a subject. One possible result of this glucose tolerance amelioration may involve maintaining or improving the glucose tolerance of the subject compared with the glucose tolerance of the subject immediately prior to the start of administration of the glucose tolerance-ameliorating agent of the present invention. Further, another possible result of the glucose tolerance amelioration may be a suppression of any decrease in the glucose tolerance of the subject compared with the glucose tolerance of the subject immediately prior to the start of administration of the glucose tolerance-ameliorating agent of the present invention.

"Administration" of the anti-obesity agent or the glucose tolerance-ameliorating agent, or "administering" the anti-obesity agent or the glucose tolerance-ameliorating agent describes the giving of the anti-obesity agent or glucose tolerance-ameliorating agent of the present invention to a subject requiring treatment, prevention or amelioration.

In this description, a "subject" requiring treatment, prevention or amelioration is an animal that is the subject of a treatment, prevention, amelioration, observation or experiment, and is preferably a mammal, and most preferably a human.

A "subject" requiring treatment, prevention or amelioration describes a subject requiring a treatment, prevention or amelioration method prescribed by a researcher, veterinary, medical doctor or other clinician.

The route of administration of the anti-obesity agent or glucose tolerance-ameliorating agent of the present invention may be either oral or parenteral, but is preferably oral. Examples of parenteral administration include transrectal administration and the like.

There are no particular limitations on the dose of the anti-obesity agent or glucose tolerance-ameliorating agent of the present invention, and the dose may be determined appropriately in accordance with the desired anti-obesity effect or glucose tolerance amelioration effect, with due consideration of the anti-obesity action or glucose tolerance-ameliorating action of the low CLA conversion *B. breve* being used and the route of administration.

For example, in those cases where *B. breve* MCC 1274 and/or *B. breve* ATCC 15700 is used as the active ingredient and administration is performed orally, the usual daily dose that is effective for the treatment or prevention of obesity or the amelioration of glucose tolerance, calculated as the bacterial count per 1 kg of body weight (CFU/kg body weight), is preferably $1 \times 10^6$ CFU/kg body weight or greater, and is more preferably $1 \times 10^8$ CFU/kg or greater.

The anti-obesity agent or glucose tolerance-ameliorating agent of the present invention may be administered in a single daily dose, or administered on a plurality of occasions.

The anti-obesity agent or glucose tolerance-ameliorating agent of the present invention may be produced in any predetermined dosage form in accordance with the administration method being used.

Examples of the dosage form of the anti-obesity agent or glucose tolerance-ameliorating agent of the present invention, in the case of oral administration, include solid formulations such as powders, granules, tablets and capsules, and liquid formulations such as syrups, suspensions and emulsions. Further, in the case of parenteral administration, examples of the dosage form include suppositories, ointments and sprays.

Production of these formulations can be conducted using conventional methods, in accordance with the dosage form.

During production, the formulation may be composed solely of the active ingredient, or may also include an appropriate pharmaceutical carrier.

In those cases where a pharmaceutical carrier is added, there are no particular limitations on the blend amount of the active ingredient within the anti-obesity agent or glucose tolerance-ameliorating agent of the present invention, and this amount may be determined appropriately in accordance with the dosage form, such as a powder, tablet or capsule. The bacterial content is typically within a range from $1 \times 10^6$ to $1 \times 10^{12}$ CFU/g, is preferably from $1 \times 10^8$ to $1 \times 10^{12}$ CFU/g, and is more preferably from $1 \times 10^{10}$ to $1 \times 10^{12}$ CFU/g.

As the pharmaceutical carrier, any conventional pharmaceutically acceptable organic or inorganic carrier may be used, depending on the dosage form.

For example, in the case of solid formulations, examples of the carrier include excipients, binders, disintegrants, lubricants, stabilizers and corrective agents and the like.

Examples of the excipients include sugar derivatives such as lactose, sucrose, glucose, mannitol and sorbitol, starch derivatives such as corn starch, potato starch, α-starch, dextrin and carboxymethyl starch, cellulose derivatives such as crystalline cellulose, hydroxypropyl cellulose, hydroxypropylmethyl cellulose, carboxymethyl cellulose and carboxymethylcellulose calcium, as well as gum arabic, dextran, pullulan, silicate derivatives such as light anhydrous silicic acid, synthetic aluminum silicate and magnesium aluminometasilicate, phosphate derivatives such as calcium phosphate, carbonate derivatives such as calcium carbonate, and sulfate derivatives such as calcium sulfate.

Examples of the binders include, in addition to the excipients mentioned above, gelatin, polyvinylpyrrolidone and magrogol.

Examples of the disintegrants include, in addition to the excipients mentioned above, chemically-modified starch or cellulose derivatives such as croscarmellose sodium, carboxymethyl starch sodium and cross-linked polyvinyl pyrrolidone.

Examples of the lubricants include talc, stearic acid, metal stearates such as calcium stearate and magnesium stearate, colloidal silica, waxes such as bee gum and spermaceti wax, boric acid, glycol, carboxylic acids such as fumaric acid and adipic acid, sodium carboxylates such as sodium benzoate, sulfates such as sodium sulfate, leucine, lauryl sulfates such as sodium lauryl sulfate and magnesium lauryl sulfate, silicates such as silicic acid anhydride and silicic acid hydrate, and starch derivatives.

Examples of the stabilizers include para-hydroxybenzoic acid esters such as methylparaben and propylparaben, alcohols such as chlorobutanol, benzyl alcohol and phenylethyl alcohol, benzalkonium chloride, acetic anhydride and sorbic acid.

Examples of the corrective agents include sweeteners, acidulants and fragrances.

In the case of liquid formulations for oral administration, examples of the carrier include solvents such as water, and corrective agents.

The anti-obesity agent or glucose tolerance-ameliorating agent of the present invention may be added to any of various pharmaceutical products, foodstuffs or nutritional products or the like.

An anti-obesity food or beverage of the present invention contains the anti-obesity agent of the present invention described above. By ingesting the anti-obesity food or beverage, a similar effect is obtained to that achieved by administering the anti-obesity agent of the present invention.

The anti-obesity food or beverage of the present invention is also effective for shaping up or dieting by suppressing increases in body fat or reducing body fat.

Although there are no particular limitations on the amount of the anti-obesity agent within the anti-obesity food or beverage of the present invention, an amount that enables a daily dose of the low CLA conversion *B. breve* that provides an effective anti-obesity effect to be ingested without any particularly difficulty is preferred, and the amount of the low CLA conversion *B. breve* is typically within a range from $1 \times 10^6$ to $1 \times 10^{12}$ CFU/g, is preferably from $1 \times 10^8$ to $1 \times 10^{12}$ CFU/g, and is more preferably from $1 \times 10^{10}$ to $1 \times 10^{12}$ CFU/g.

The anti-obesity food or beverage of the present invention may be produced using the anti-obesity agent and other components acceptable for inclusion within food and beverages as raw materials, or may be produced by adding the anti-obesity agent of the present invention to an existing food or beverage containing other components.

For example, if the anti-obesity food or beverage of the present invention is a fermented milk product, then the anti-obesity food or beverage may be produced by adding a low CLA conversion *B. breve* to a fermented milk, or may be a fermented milk produced by using the low CLA conversion *B. breve* as a starter.

There are no particular limitations on the other components included within the food or beverage, provided the components have been approved for addition to foods and beverages in food regulations such as the Food Sanitation Act, and do not impair the anti-obesity action. Examples of components that may be included within the food or beverage include sugars such as dextrin and starch, proteins such as gelatin, soy protein, and corn protein, amino acids such as alanine, glutamine and isoleucine, polysaccharides such as cellulose and gum arabic, and oils and fats such as soybean oil and medium-chain fatty acid triglycerides.

There are no particular limitations on the form of the food or beverage, which includes any form of edible composition composed of the low CLA conversion *B. breve* and a carrier that is acceptable for inclusion within food and beverages. Specific examples include all manner of food and beverage forms, including solid foods such as bread, chewing gum, cookies, chocolate, confectionery and cereals, jam-base, cream-based and gel-based foods such as jam, ice cream, yogurt and jelly, and beverages such as juices, coffee and cocoa. Further, the low CLA conversion *B. breve* may also be added to flavorings and food additives and the like.

In those cases where the anti-obesity food or beverage of the present invention is a fermented milk product produced using the low CLA conversion *B. breve* as a starter, the low CLA conversion *B. breve* may be used alone during fermentation, or a mixed incubation may be performed using the low CLA conversion *B. breve* and another starter.

Examples of these other starters include those starters typically used in the production of fermented milk products, such as other bacteria of the genus *Bifidobacterium* (such as the Bifidobacteria: *B. pseudocatenulatum, B. catenulatum, B. bifidum, B. longum, B. infantis* and *B. adolescentis*), and other conventional lactic acid bacteria typically used as starters for fermented milk products. Specific examples of these lactic acid bacteria include *Streptococcus thermophilus, Lactococcus lactis, Lactobacillus bulgaricus, Lactobacillus casei* and *Lactobacillus gasseri*.

The fermented milk can be produced using a conventional method. One example of a method of producing a fermented milk is outlined below.

First, a raw material mix containing the raw material milk is prepared. Besides the raw material milk, the raw material mix may also contain other components such as oils and fats, sugars and water, according to need. For example, a raw material containing fat such as butter or cream may be added as a fat component. Examples of sugars that may be added include typical sweeteners such as sucrose, maltose, glucose, fructose, dextrin and reduced maltose. In those cases where a hard yogurt is to be produced, pre-swollen gelatin and/or a dissolved agar solution may be added. In those cases where a soft yogurt is to be produced, whey protein and/or a polysaccharide thickener may be added. In those cases where a drink yogurt is to be produced, high methoxyl pectin may be added in an amount of 0 to 0.3% by mass as a stabilizer, although it is preferable that absolutely no high methoxyl pectin is added.

There are no particular limitations on the method used for producing the raw material mix, and for example, the other components that are included according to need may be added to the raw material milk, and the resulting mixture then stirred and mixed to obtain the raw material mix.

The blend ratio of the raw material milk within the raw material mix, calculated as a non-fat solid fraction, is preferably within a range from 1 to 15% by mass, and more preferably from 8 to 15% by mass.

Subsequently, the raw material mix is subjected to a heat sterilization treatment. Although there are no particular limitations on the sterilization method or the heating conditions, a heating temperature of 80 to 140° C. is preferred, and the heating time is preferably within a range from 5 to 15 minutes in the case of a batch treatment, or within a range from 2 seconds to 15 minutes in the case of an HTST method.

The heat-sterilized raw material mix is then inoculated with the starter bacteria, and fermentation is performed. The fermentation conditions, including the amount of the starter used for inoculation, the fermentation temperature and the fermentation time may be set appropriately in accordance with factors such as the type of starter employed, and the variety and properties of the fermented milk product being produced. Depending on the form of the product, following inoculation with the starter, the mixture may be placed inside a container for fermentation, or the fermentation may be conducted in a fermentation tank.

Following fermentation, the mixture is cooled rapidly to obtain the fermented milk product. Depending on the type of product and the product properties, a step of homogenizing the product following cooling, or a step of adding other raw materials such as flavorings following cooling may be performed.

The fermented milk obtained in this manner may be used, without further heat sterilization, as a live bacteria-type product that enables ingestion of live bifidobacteria. Live bacteria-type products are stored, transported and marketed at a low temperature of not more than 10° C., and preferably a temperature of 0 to 5° C.

The anti-obesity food or beverage according to the present invention is preferably marketed as a food or beverage that indicates its use for anti-obesity applications, for example by employing the expression "anti-obesity" or "food (or beverage) having an anti-obesity effect".

It should be noted that the expression used for the type of indication described above is not limited to the phrase "anti-obesity", and needless to say, any other expressions that indicate an anti-obesity effect are also included within the scope of the present invention. Examples of such other expressions may include "obesity prevention effect", "obesity improvement effect", "weight increase suppression effect", "body fat increase suppression effect" or "dietary effect", and the food or beverage may be marketed with one or more of these expressions indicated on the product.

Further, in a similar manner, the food or beverage may also be marketed as a food or beverage that indicates its use in preventing and/or ameliorating lifestyle diseases for which obesity is a known cause, such as hyperlipidemia, high blood pressure and diabetes.

The food or beverage for ameliorating glucose tolerance according to the present invention is preferably marketed as a food or beverage that openly indicates its use for glucose tolerance amelioration, for example by employing the expression "for glucose tolerance amelioration" or "food (or beverage) having a glucose tolerance amelioration effect".

It should be noted that the expression used for the type of indication described above is not limited to the phrase "for glucose tolerance amelioration", and needless to say, any other expressions that indicate a glucose tolerance amelioration effect are also included within the scope of the present invention.

Further, in a similar manner, the food or beverage may also be marketed as a food or beverage that indicates its use in preventing and/or ameliorating lifestyle diseases for which a reduction in glucose tolerance or insulin resistance is a known cause, such as diabetes and other lifestyle diseases.

The action associated with the above term "indicate" includes all actions for informing consumers about the above-described use, and any displays reminding consumers of the above-described use or allowing consumers to recognize the above-described use by analogy fall within the scope of the "indication" according to the present invention, irrespective of the purpose of the indication, content of the indication, or object or medium or the like of the indication. However, the indication is preferably given using an expression that enables consumers to directly recognize the above-mentioned use. Specific examples of the indication include actions of indicating the above-mentioned use on commercial products relating to the food or drink according to the present invention or packages of the commercial products, actions of assigning, delivering, displaying for the purpose of assigning or delivering, or importing the commercial products or packages thereof with an indication indicating the above-described use, and actions of indicating the above-described use on advertisements, price lists or business papers relating to the products by displaying or distributing them, or indicating the use within information including such advertisements, price lists or business papers and providing that information by an electromagnetic method (such as the Internet).

The content of the indication (indicated content) is preferably approved by the government or the like of the country in question (for example, an indication in a form based on an approval granted on the basis of any of various systems established by the government of that country), and such indicated content is preferably attached to packages, containers, catalogs, advertising media used at sales sites such as pamphlets and POPs, and other documents.

Furthermore, other examples of the indication include indications as a health food, functional food, enteral food, food for special dietary use, food with health claims, food for specified health uses, food with nutrient functional claims, and quasi-drug. Particularly in the case of Japan, other examples include indications approved by the Ministry of Health, Labor and Welfare, such as indications approved on the basis of the food system for specified health uses and other similar systems. Examples of the latter include indications as food for specified health uses, indications as qualified food for specified health uses, indications of influence on body structures or functions, and indications of reduction in disease risk claims. More specifically, typical examples thereof include indications as food for specified health uses (especially, indications of use for health) prescribed in the enforcement regulations of Health Promotion Law (Ministerial ordinance No. 86, Ministry of Health, Labor and Welfare, Japan, Apr. 30, 2003) and similar indications.

EXAMPLES

The present invention is described in more detail below using a series of test examples and examples, but the present invention is in no way limited by the following examples.

Test Example 1

Measurement of CLA Conversion Rate

Bacterial cells of *B. breve* (MCC 1274 or ATCC 15700) at a concentration of $2 \times 10^7$ CFU/mL were suspended in an MRS medium (MRS (de Man Rogossa Sharpe) broth, a Difco (registered trademark) product, manufactured by Becton Dickinson and Company) containing an added concentration of LA of 500 μg/mL, and the medium was then incubated for 48 hours at 37° C.

Subsequently, the supernatant was recovered, a volume of isopropyl alcohol twice that of the supernatant was added to the supernatant and mixed, a volume of hexane 1.5 times that of the supernatant was then added to the mixture, and after mixing for 3 minutes, the mixture was left to settle and the hexane layer was recovered. The absorbance of the hexane layer at 233 nm was measured, and using a calibration curve prepared using standard materials (cis-9, trans-11 conjugated linoleic acid), the CLA concentration (μg/mL) within the hexane layer was determined and the amount of CLA (μg) contained within the above supernatant was calculated.

Meanwhile, to the residue left following recovery of the supernatant was added and mixed an amount of distilled water 5 times that of the residue, thus forming a suspension. A volume of isopropyl alcohol twice that of the suspension was added to the suspension and mixed, a volume of hexane 1.5 times that of the suspension was then added to the mixture, and after mixing for 3 minutes, the mixture was left to settle and the hexane layer was recovered. The CLA concentration (μg/mL) within the hexane layer was determined in the same manner as that described above, and the amount of CLA (μg) contained within the residue was calculated.

The total of the amounts of CLA contained within the supernatant and the residue was recorded as the "amount of produced CLA", and the conversion rate (%) from LA into CLA was determined from the formula below. The results are shown in Table 2.

Conversion rate (%)=(amount of produced CLA/amount of added LA)×100

As shown by the results below, the two strains (MCC 1274 and ATCC 15700) both exhibited CLA conversion rates of 10% or less.

TABLE 2

| | CLA conversion rate (%) |
|---|---|
| MCC 1274 | 10.0 |
| ATCC 15700 | 5.0 |

Test Example 2

Investigation of Effects of Administering Low CLA Conversion *B. breve* to Model Mice having Diet-Induced Obesity 18 C57BL/6J male mice were used, with 6 mice grouped into each of three groups. After administering a 45% high-fat diet over a 4-week period to make the mice obese, a 10% skim milk powder was mixed with the feed of a control group, a 10% skim milk powder containing the bacterial strain MCC 1274 suspended therein was mixed with the feed of a MCC 1274 administration group, and a 10% skim milk powder containing the bacterial strain ATCC 15700 suspended therein was mixed with the feed of a ATCC 15700 administration group, and each group was fed for a further 8 weeks. At this time, the amount of the MCC 1274 or ATCC 15700 added to the milk powder by suspension therein was set so that the amount of the *B. breve* ingested per day was approximately 1 billion bacteria per mouse. Further, a feed containing 22% by mass of fatty acids (of which the amount of linoleic acid was approximately 3.1% by mass) was used as the feed.

During the test period, only the body weight of each mouse was measured, and then following completion of the test, the mice were killed and dissected, and the body weight and the weight of the epididymal adipose tissue were measured.

Figure 1:
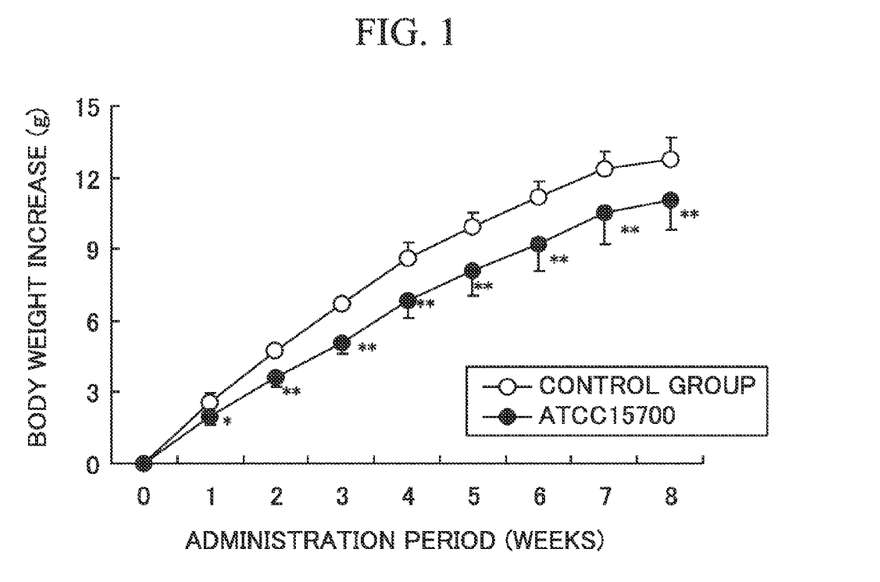
FIG. 1 is a graph illustrating the trends in body weight increase for a control group and a *Bifidobacterium breve* ATCC 15700 administration group in test example 2.
Figure 2:
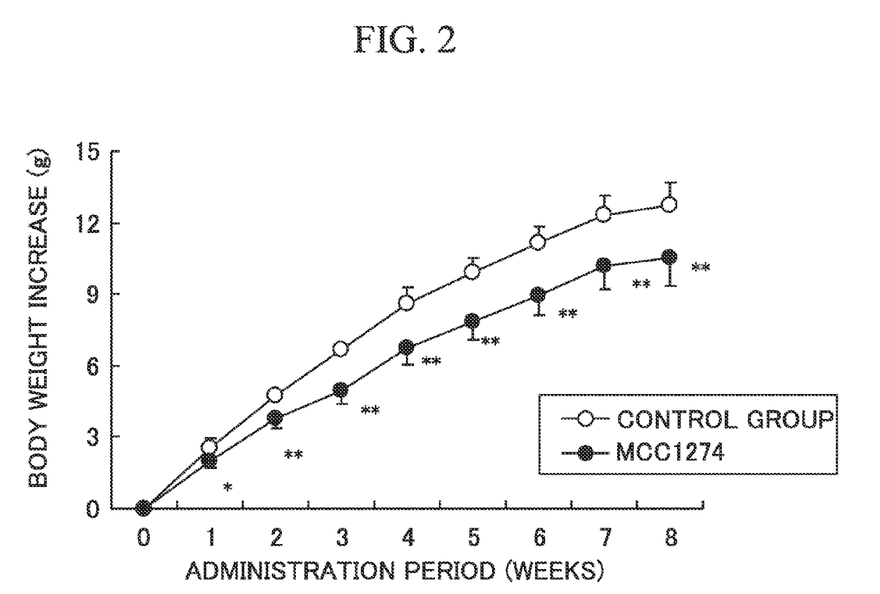
FIG. 2 is a graph illustrating the trends in body weight increase for a control group and a *Bifidobacterium breve* MCC 1274 administration group in test example 2.

The trends in body weight increase during the test period are shown in FIG. 1 and FIG. 2. The results in FIG. 1 and FIG. 2 reveal that although the body weight increased in all the groups, compared with the control group, the 2 groups that were administered with the MCC 1274 or ATCC 15700 exhibited significant suppression of the increase in body weight (compared with the control group, the body weight in the test groups decreased by approximately 18% or more, indicating a significant difference at p<0.05).

Figure 3:
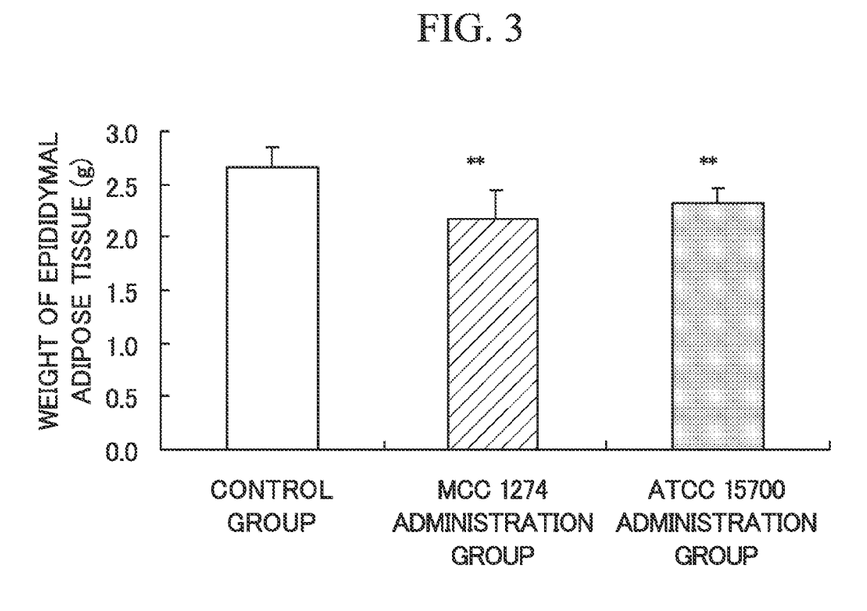
FIG. 3 is a graph illustrating the results of measuring the weight of epididymal adipose tissue in test example 2.

Further, the weight of epididymal adipose tissue upon dissection is shown in FIG. 3. The results in FIG. 3 reveal a weight of epididymal adipose tissue upon dissection of 2.66 g for the control group, 2.17 g for the MCC 1274 administration group, and 2.32 g for the ATCC 15700 administration group, confirming that the MCC 1274 and the ATCC 15700 suppressed increases in the adipose weight (compared with the control group, the weight of adipose tissue decreased by 18.4% in the MCC 1274 group and 12.8% in the ATCC 15700 group, which are significant differences at p<0.05).

Based on the above results it was clear that the bacterial strains *B. breve* MCC 1274 and *B. breve* ATCC 15700 had an anti-obesity action, including a body weight increase-suppressing action and a body fat increase-suppressing action, and in particular, were able to suppress increases in (accumulation of) body fat.

Figure 4:
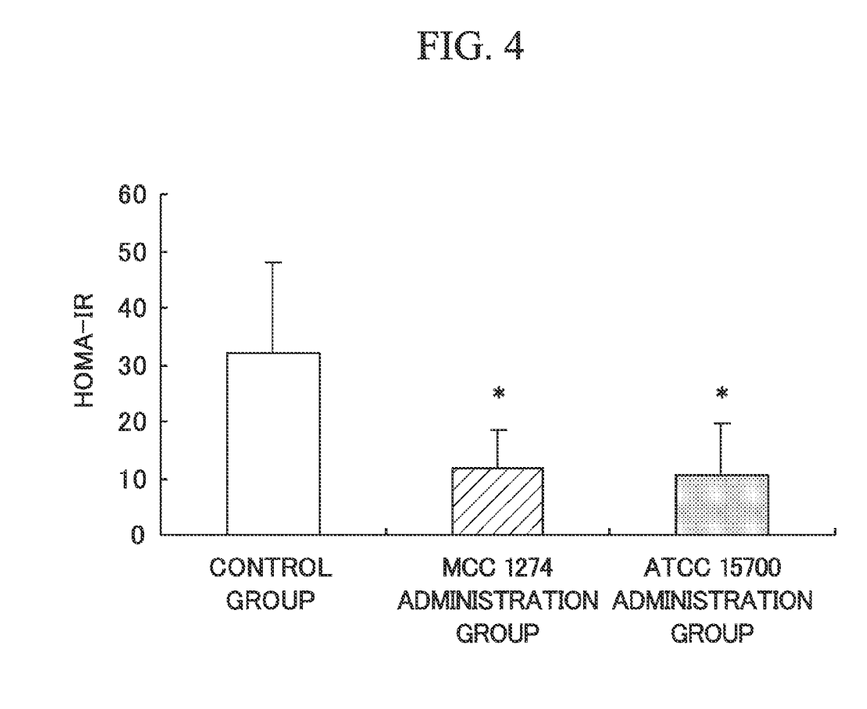
FIG. 4 is a graph illustrating the results of measuring the HOMA-IR (Homeostasis Model Assessment of Insulin Resistance) value in test example 2.

Moreover, at the time of dissection, the blood insulin level and the blood sugar level were also measured by conventional methods, and from the resulting measurement values, the HOMA-IR value, which acts as an indicator of insulin resistance, was calculated using the numerical formula (1) below.

$$\text{HOMA-IR value} = \text{blood sugar level (mg/dL)} \times \text{blood insulin level (μIU/mL)} \div 405 \qquad (1)$$

As shown in FIG. 4, the results revealed a value of 32.10 for the control group, a value of 11.87 for the MCC 1274 administration group, and a value of 10.55 for the ATCC 15700 administration group, confirming that *B. breve* MCC 1274 and ATCC 15700 exhibited amelioration of glucose tolerance and amelioration of insulin resistance. (a significant difference at p<0.05 compared with the control group).

From the above results it was evident that the *B. breve* was not only free of the side effects associated with conjugated linoleic acid, but also ameliorated the glucose tolerance and the insulin resistance.

As indicated by the above results, low CLA conversion *B. breve* having a CLA conversion rate of not more than 10% exhibited an anti-obesity action, including a body weight increase-suppressing action and a body fat increase-suppressing action, in mice with dietary-induced obesity.

In the above Test Example 2, if it is assumed that the LA (3.1%) within the feed was converted into CLA by the low CLA conversion *B. breve*, then the amount of CLA within the feed would be no more than 0.3%. In order to achieve an anti-obesity effect or a reduction in body fat due to CLA in dietary-induced obese mice, at least 0.5% of CLA must be mixed with the feed (see Non-Patent Document 5), and considering this fact, the low CLA conversion *B. breve* exhibits an anti-obesity action that is independent of CLA.

Example 1

Powder Formulation

A reconstituted skim milk powder medium (containing 13% by weight of skim milk powder and 0.5% by weight of a yeast extract) was sterilized at 95° C. for 30 minutes. Subsequently, the medium was inoculated with a seed culture of *B. breve* ATCC 15700 and then incubated for 16 hours at 37° C. The resulting incubated product was freeze-dried to obtain a *B. breve* ATCC 15700 powder formulation. The bacterial count of *B. breve* ATCC 15700 contained within the obtained powder formulation was $8.5 \times 10^{10}$ CFU/g.

This powder formulation can be used, without further modification, within an anti-obesity agent, anti-obesity food or beverage, glucose tolerance-ameliorating agent or food or beverage for ameliorating glucose tolerance according to the present invention.

Example 2

Powder Formulation

With the exception of using *B. breve* MCC 1274 instead of the *B. breve* ATCC 15700, a powder formulation was prepared in the same manner as Example 1. The bacterial count of *B. breve* MCC 1274 contained within the obtained powder formulation was $5.5 \times 10^{10}$ CFU/g.

This powder formulation can be used, without further modification, within an anti-obesity agent, anti-obesity food or beverage, glucose tolerance-ameliorating agent or food or beverage for ameliorating glucose tolerance according to the present invention.

Example 3

Yogurt 1000 mL of an 11% (w/w) skim milk powder medium containing 0.5% (w/w) of a yeast extract was sterilized at 90° C. for 30 minutes, and the medium was then inoculated with 100 mL of a seed culture of *B. breve* ATCC 15700 and incubated for 16 hours at 37° C.

In a separate preparation, 1500 mL of a 10% (w/w) reconstituted skim milk medium was sterilized at 90° C. for 30 minutes, and the medium was then inoculated with 50 mL of a mixed culture of *Streptococcus thermophilus* (manufactured by Chr. Hansen A/S) and *Lactobacillus bulgaricus* (manufactured by Chr. Hansen A/S) and incubated for 5 hours at 42° C.

Further, in yet another preparation, 50 L of a raw milk containing 3.0% (w/w) of milk fat and 9% (w/w) of non-fat milk solids was heated to 70° C., homogenized at a pressure of 15 MPa, sterilized at 90° C. for 10 minutes, and then cooled to 40° C. This sterilized base was inoculated with 750 mL of the previously incubated *B. breve* ATCC 15700 culture and 300 mL of the incubated mixed culture of *Streptococcus thermophilus* and *Lactobacillus bulgaricus*, the resulting mixture was used to fill a multilayer container (volume: 500 mL) sandwiched by aluminum. The container was sealed and incubated at 37° C. until the pH reached 4.6, and was then immediately cooled.

The thus obtained yogurt had a lactic acid value of 0.81%, and contained $1.1 \times 10^8$ CFU/mL of the *B. breve* ATCC 15700.

This yogurt can be used, without further modification, as an anti-obesity food or beverage or a food or beverage for ameliorating glucose tolerance according to the present invention.

Example 4

Yogurt

With the exception of using *B. breve* MCC 1274 instead of the *B. breve* ATCC 15700, a yogurt was prepared in the same manner as Example 3.

The resulting yogurt contained $8.5 \times 10^7$ CFU/mL of the *B. breve* MCC 1274.

This yogurt can be used, without further modification, as an anti-obesity food or beverage or a food or beverage for ameliorating glucose tolerance according to the present invention.

INDUSTRIAL APPLICABILITY

The present invention is able to provide an anti-obesity agent and a glucose tolerance-ameliorating agent that are effective for the prevention or treatment of obesity or the amelioration of glucose tolerance and also exhibit superior safety, as well as providing foods or beverages containing these agents. Further, the present invention is also able to provide a bacterium of the genus *Bifidobacterium*, and in particular a *Bifidobacterium breve*, that is effective for the prevention or treatment of obesity or the amelioration of glucose tolerance or insulin resistance and also exhibits superior safety, as well as providing a pharmaceutical composition containing this bacterium.

Accession Number
FERM BP-11175

The invention claimed is:

1. An isolated bacterial strain that is *Bifidobacterium breve* MCC 1274 (FERM BP-11175).

2. A pharmaceutical composition comprising *Bifidobacterium breve* MCC 1274 (FERM BP-11175) and a pharmaceutically acceptable carrier.

3. An anti-obesity food or beverage, or a food or beverage for ameliorating glucose tolerance, comprising the pharmaceutical composition according to claim 2.

* * * * *